United States Patent
Johnson et al.

(10) Patent No.: US 8,907,121 B2
(45) Date of Patent: Dec. 9, 2014

(54) METHYL METHACRYLATE PURIFICATION PROCESS

(75) Inventors: David William Johnson, Redcar (GB); Trevor Huw Morris, Redcar (GB)

(73) Assignee: Lucite International UK Limited, Hampshire (GB)

( * ) Notice: Subject to any disclaimer, the term of this patent is extended or adjusted under 35 U.S.C. 154(b) by 344 days.

(21) Appl. No.: 13/140,754

(22) PCT Filed: Dec. 11, 2009

(86) PCT No.: PCT/GB2009/051693
§ 371 (c)(1),
(2), (4) Date: Aug. 3, 2011

(87) PCT Pub. No.: WO2010/070325
PCT Pub. Date: Jun. 24, 2010

(65) Prior Publication Data
US 2011/0282023 A1    Nov. 17, 2011

(30) Foreign Application Priority Data

Dec. 18, 2008  (GB) .................................. 0823075.7
Jun. 18, 2009  (GB) .................................. 0910498.5

(51) Int. Cl.
*C07C 67/48* (2006.01)
*C07C 67/60* (2006.01)

(52) U.S. Cl.
CPC ..................................... *C07C 67/60* (2013.01)
USPC ......................................................... 560/218

(58) Field of Classification Search
CPC combination set(s) only.
See application file for complete search history.

(56) References Cited

U.S. PATENT DOCUMENTS

| | | | |
|---|---|---|---|
| 3,965,149 A | 6/1976 | Mahoney | |
| 4,625,059 A * | 11/1986 | Shibano et al. | 562/600 |
| 5,034,558 A * | 7/1991 | Yoshioka et al. | 560/218 |
| 5,859,104 A | 1/1999 | Becker | |
| 6,384,268 B1 | 5/2002 | Parten et al. | |

FOREIGN PATENT DOCUMENTS

| | | |
|---|---|---|
| CN | 1185459 A | 6/1998 |
| GB | 783073 A | 9/1957 |
| JP | 59-048437 A | 3/1984 |
| JP | 59-048439 A | 3/1984 |

(Continued)

OTHER PUBLICATIONS

Machine Translation of JP 200172639.*

(Continued)

*Primary Examiner* — Karl J Puttlitz
(74) *Attorney, Agent, or Firm* — Venable LLP; Keith G. Haddaway; Annette K. Kwok (57) ABSTRACT

A process for purifying methyl methacrylate (MMA) is described. The process involves contacting liquid MMA having impurities therein with a sulphonic acid resin, in the presence of formaldehyde or a suitable source of methylene or ethylene of formula I. $R^5$ and $R^6$ are independently selected from $C_1$-$C_{12}$ hydrocarbons or H; X is either O or S; n is an integer from, 1 to 100; and m is 1 or 2: The compound of formula I may be suitable source of formaldehyde.

$$R^5X \left[ \left( C H_2 \right)_m X \right]_n R^6 \quad (I)$$

18 Claims, 1 Drawing Sheet

Divinyl Ketone Removal

(56) References Cited

FOREIGN PATENT DOCUMENTS

| | | |
|---|---|---|
| JP | 11-60536 A | 3/1999 |
| JP | 2001-072639 A | 3/2001 |
| JP | 2001-072643 A | 3/2001 |
| JP | 200172639 * | 3/2001 |
| RU | 2217413 C2 | 11/2003 |
| WO | WO 99/26915 A1 | 6/1999 |
| WO | WO 2005/003063 A2 | 1/2005 |

OTHER PUBLICATIONS

Written Opinion of the Hungarian Intellectual Property Office issued in Singapore Application No. 201103759-5 dated Mar. 18, 2013.
Office Action issued in Chinese Application No. 200980150718.6 dated Apr. 1, 2013.
Office Action issued in Australian Patent Application No. 2009329327 dated Oct. 31, 2013.
Office Action issued in Chinese Patent Application No. 200980150718.6 dated Oct. 21, 2013.
Nov. 11, 2013 letter reporting Office Action issued in Mexican Patent Application No. MX/a/2011/006457.
Office Action issued in Russian Patent Application No. 2011129628/04 dated Oct. 14, 2013.
Office Action issued in Chinese Patent Application No. 200980150718.6 dated Feb. 24, 2014.
Office Action issued in Russian Patent Application No. 2011129628/04 dated Feb. 24, 2014.

* cited by examiner

METHYL METHACRYLATE PURIFICATION PROCESS

The present invention relates a to purification process, particularly to a process for purifying methyl methacrylate (MMA).

MMA is a well known chemical substance and has many uses, but largely it is used as a monomer in the production of poly-methylmethacrylate (PMMA). PMMA is often formed in thin sheets which can be moulded into a variety of shapes as required by a particular use.

It is important when preparing PMMA, that the MMA used is of the highest purity because even low levels of impurity can lead to a PMMA product which has a cloudy or dull appearance or is discoloured. Also, low levels of impurity in the MMA can lead to a change in the structural properties of the PMMA product which can have undesired effects. It is therefore important to be able to provide MMA, the monomer for PMMA, with a high degree of purity to try and reduce the occurrence of these problems.

MMA may be produced in many ways. For example, reaction of acetone cyanohydrin, methanol and concentrated sulphuric acid; oxidation of tertiary butyl alcohol to methacrolein and then to methacrylic acid followed by esterification with methanol; alternatively catalysed reactions as disclosed in EP 1,073,517. Such reactions and many others known in the art provide a stream of MMA that commonly contains impurities therein which can cause problems such as those discussed above when the MMA is polymerised to form PMMA. Consequently, it is usual to attempt to purify the MMA stream before polymerisation.

It is known to separate impurities having boiling points which are significantly different to the MMA by distillation. However, such a separation method is difficult to achieve where the impurities have a similar boiling point to the MMA.

Japanese patent 58-183641 discloses the use of an acid catalyst to treat impurities in crude methyl methacrylate.

Japanese patent application 63-127952 teaches the use of sulfonic acid group containing compounds to treat high purity methyl methacrylate.

U.S. Pat. No. 4,625,059, to Mitsubishi Petrochemical shows the use of acid ion exchange resin fixed beds to remove impurities from crude MMA.

Therefore, crude MMA made by a number of process routes contains a wide range of impurities which are difficult to remove by distillation. MMA produced by the condensation of formaldehyde with methyl propionate contains additionally other as yet undefined impurities such as colour forming compounds which are not disclosed in prior art MMA production processes.

It is an object of aspects of the present invention to provide a solution to the removal of these or other impurities by purification of MMA.

According to a first aspect of the present invention there is provided a process for purifying methyl methacrylate (MMA) comprising contacting liquid MMA having impurities therein with a sulphonic acid resin, in the presence of formaldehyde or suitable source of methylene or ethylene of formula I as defined below:

where $R^5$ and $R^6$ are dependently selected from $C_1$-$C_{12}$ hydrocarbons, preferably, $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H;

X is either O or S, preferably, O;

n is an integer from 1 to 100, preferably, 1 to 10, more preferably 1 to 5, especially, 1-3;

and m is 1 or 2, preferably 1.

In a particularly preferred embodiment the compound of formula I is derived from formaldehyde in the presence of methanol and/or water. In such a case, the compound of formula I may be defined as a suitable source of formaldehyde.

For the avoidance of doubt, a suitable source of formaldehyde includes any equilibrium composition which may provide a source of formaldehyde. Examples of such include but are not restricted to methylal (1,1 dimethoxymethane), polyoxymethylenes —$(CH_2$—$O)_i$— wherein i=1 to 100 formalin (formaldehyde, methanol, water) and other equilibrium compositions such as a mixture of formaldehyde, methanol and methyl propionate.

Typically, the polyoxymethylenes are higher formals of formaldehyde and methanol $CH_3$—O— $(CH_2$—$O)_i$—$CH_3$ ("formal-i"), wherein i=1 to 100, preferably, 1-5, especially 1-3, or other polyoxymethylenes with at least one non methyl terminal group. Therefore, the source of formaldehyde may also be a polyoxymethylene of formula $R_1$—O—$(CH2$-$O$—$)_iR_2$, where $R_1$ and $R_2$ may be the same or different groups and at least one is selected from a $C_2$-$C_{10}$ alkyl group, for instance $R_1$=isobutyl and $R_2$=methyl.

Preferably, the formaldehyde or the amount of formaldehyde that can be liberated from a suitable source of formaldehyde is present in an amount between 0.01 and 0.1 weight percent relative to the weight of liquid MMA.

Preferably, the suitable source of formaldehyde is selected from 1,1 dimethoxymethane, higher formals of formaldehyde and methanol for example $CH_3$—O—$(CH_2$—$O)_i$—$CH_3$ where i=2 or more as set out above, formalin or a mixture comprising formaldehyde, methanol and methyl propionate.

Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol:water in the ratio 30 to 60%:0.03 to 20%:35 to 60% by weight. Most preferably, by the term formalin is meant a mixture of formaldehyde:methanol:water in the ratio 35 to 55%:0.05 to 18%: 42 to 53% by weight.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

Preferably, the suitable source of formaldehyde has a boiling point in the range of 69 to 73° C. at 0.75 bar absolute.

Preferably, the formaldehyde or source thereof is mixed with the impure liquid MMA prior to contact with the sulphonic acid resin. Typically, in a continuous or semi-continuous process, an impure liquid MMA stream is mixed with a stream containing the formaldehyde or source thereof to form a combined liquid stream prior to contact with the sulphonic acid resin. The formaldehyde is therefore present in an amount between 0.01 and 0.1 weight percent in the combined liquid stream.

Alternatively, or additionally the formaldehyde source may be present as an impurity in the MMA, preferably as a close boiling impurity prior to contact with the sulphonic acid resin. In such cases the passing of the impure MMA over the ion exchange resin bed acts to remove or reduce the concentration of the formaldehyde source and or change its composition to a heavy or a light component which can be readily separated from MMA by distillation.

Preferably the close boiling impurity present as an impurity in the MMA is formal-2 ($CH_3$—O—($CH_2$—O)$_2$—$CH_3$).

Preferably the light component with respect to separation from MMA is dimethoxymethane. Preferably the dimethoxymethane is separated from the MMA by distillation.

Preferably, the purification process of the invention is performed at a temperature between 25 and 100° C. More preferably, the process is carried out at a temperature between 40 and 90° C. More preferably, the process is carried out at a temperature between 50 and 80° C. Most preferably, the process is carried out at a temperature between 50 and 70° C.

Preferably, the sulphonic acid resin comprises a packed bed. Preferably, the sulphonic acid resin comprises a strongly acidic, macroporous, polymer based resin. Most preferably, the sulphonic acid resin comprises a crosslinked polystyrene resin in spherical bead form with bead size 0.4 to 1.64 mm, with between 0.5 and 3.0 equivalents per liter of sulphonic acid groups (preferably between 0.7 and 2.5) with a large pore structure with mean pore diameter between 15 nm and 90 nm (preferably between 20 nm and 70 nm), surface area between 15 $m^2g^{-1}$ and 100 $m^2g^{-1}$ (preferably between 20 $m^2g^{-1}$ 80 $m^2g^{-1}$) and a pore volume measured by the extent of water retention per unit of wet resin of between 30 and 80% (preferably 40-70%). Preferably the acidic ion exchange resin is a macroreticular resin.

Preferably, at least one carboxylic acid ester is also present in the purification process. Preferably, the or each carboxylic acid ester is selected from the methyl, ethyl or propyl ester of any straight or branched $C_2$ to $C_6$ carboxylic acid. More preferably, the or each at least one carboxylic acid is selected from the methyl or ethyl ester of any branched or unbranched $C_2$ to $C_4$ carboxylic acid. Examples of suitable carboxylic acid esters include but are not restricted to methyl propionate, ethyl propionate, propyl propionate, methyl butanoate, methyl isobutyrate, ethyl butanoate, propyl butanoate, butyl butanoate. In a preferred embodiment, methyl propionate or methyl isobutyrate are also present in the purification process.

Typically, in a continuous or semi-continuous process the at least one carboxylic acid ester is already present in the impure liquid MMA stream prior to contact with the sulphonic acid resin. Typically, therefore, in such embodiments, the at least one carboxylic acid ester forms part of the combined liquid stream.

Typically, the impurities have a boiling point which renders separation by distillation ineffective. Typically, the impurities have a boiling point within 15° C. of MMA. More typically, the impurities have a boiling point within 10° C. of MMA. Most typically, the impurities have a boiling point within 5° C. of MMA. Generally, the impurities have a boiling point which is approximately the same as MMA i.e. within 1 or 2° C. Impurities may have boiling points as pure components which are more than 15° C. of MMA if they exhibit non ideal distillation behaviour, in combination with either MMA or with one or more impurities or with MMA and another impurity such physical effects making the impurity very difficult to separate from MMA by distillation. Examples of such physical effects are the formation of high or low boiling azeotropes.

The invention has been found to be particularly useful in the removal of several impurities in the impure MMA liquid. It has been found that the impurities may comprise isobutyraldehyde either as isobutyraldehyde or in a compound which regenerates isobutyraldehyde when exposed to the sulphonic acid ion exchange resin. Examples of such compounds include the mono or di-acetals of isobutyraldehyde with a $C_1$ to $C_6$ branched or non-branched alcohol, in particular 2,2-dimethoxypropane, and methallyl alcohol.

Removal of isobutyraldehyde using the formaldehyde/resin combination is advantageous even though isobutyraldehyde would separate from the MMA as a lower boiling impurity. Removing isobutyraldehyde in the low boiling impurity (lights) column runs the risk of polymerisation initiation by isobutyraldehyde/oxygen in the lights column overheads which are predominantly MMA and have to be fed with oxygen for the polymerisation stabilisers to be effective.

In addition, recycling of isobutyraldehyde causes slow conversion to isobutanol over the catalyst. Isobutanol escapes into the MMA pure product both reducing the specification and also providing a problem with thick sheet as it reacts with polymerisation initiators, thereby increasing the demand for such initiators which are invariably coloured in both their unreacted and reacted (with isobutanol) forms. This is an issue with aquarium grades and some others where very low levels of initiators are demanded.

Further impurities that have been advantageously removed include optionally substituted $C_4$-$C_{20}$ dienes. The invention has been found to be particularly useful for such dienes. Useful substituted dienes that can be removed are $C_{1-6}$ monotetra alkyl $C_4$-$C_{20}$ dienes, such as $C_4$-$C_8$ dienes, for example, mono or dialkyl hexadienes. Examples of dienes have been found to include but are not restricted to any of the following: 2,5-dimethyl-2,4-hexadiene; 2,5-dimethyl-1,5-hexadiene, 2-methyl-1,5-hexadiene; trans 2-methyl-2,4-hexadiene; cis 2-methyl-2,4-hexadiene; 2-methyl-3,5-hexadiene; 2-methyl-1,3-hexadiene; 2,5-dimethyl-1,3-hexadiene and 1,6-heptadiene.

In addition, the impurities may also typically comprise optionally substituted $C_6$-$C_{20}$ trienes. Examples of trienes include but are not restricted to any of the following: heptatriene, cycloheptatriene.

The invention has been found to be especially efficient for $C_4$-$C_{20}$ dienes or $C_6$-$C_{20}$ trienes with one or more substituted, preferably, alkyl, more preferably, $C_{1-6}$ alkyl substituted, internal enyl carbons or di-substituted, preferably, alkyl, more preferably, $C_{1-6}$ alkyl substituted, terminal enyl carbons which enyl carbons are thereby capable of forming tertiary carbocations. Most preferably, the invention is for the removal of $C_4$-$C_{20}$ dienes, optionally, substituted as defined above. Particularly preferred dienes for removal by the present invention are: trans 2-methyl-2,4-hexadiene; c is 2-methyl-2,4-hexadiene; 2-methyl-3,5-hexadiene; 2-methyl-1,3-hexadiene; 2,5-dimethyl-1,3-hexadiene and 1,6-heptadiene, in particular trans 2-methyl-2,4-hexadiene and cis 2-methyl-2,4-hexadiene.

Other impurities that may be removed by the practice of the present invention also typically comprise optionally substituted unsaturated aldehydes and ketones. Examples of such aldehyde or ketone compounds include R'C=OR" wherein R' can be hydrogen, optionally substituted alkyl, alkenyl or aryl more preferably, $C_{1-6}$ alkyl, $C_{1-6}$ alkenyl or aryl and R" can be optionally substituted alkyl, alkenyl or aryl, more preferably, $C_{1-6}$ alkyl, $C_{1-6}$ alkenyl or phenyl.

In addition, 2-methylene-3-buten-al may also be present and removed by the process of the invention. Advantageously, this impurity may otherwise be colour forming in the MMA.

Suitable further impurities include: divinyl ketone, ethyl vinyl ketone, diethyl ketone, ethyl isopropenyl ketone, 3-methylene 1-hexen-4-one, methacrolein, isobutanol, toluene, and pentenals such as 3-pentenal. Preferred further impurities which can be removed by the practice of the present invention are ethyl vinyl ketone and divinyl ketone.

Accordingly, the present invention is particularly beneficial for the removal of trans 2-methyl-2,4-hexadiene; cis 2-methyl-2,4-hexadiene; ethyl vinyl ketone and divinyl ketone.

A suitable process for preparing the MMA prior to purification by contact with formaldehyde or a source of methylene or ethylene comprises contacting methyl propionate with a suitable source of methylene of formula I as defined below:

where $R^5$ and $R^6$ are independently selected from $C_1$-$C_{12}$ hydrocarbons, preferably, $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H;

X is either O or S, preferably, O;

n is an integer from to 100, preferably, 1 to 10, more preferably 1 to 5, especially, 1-3;

and m is 1;

in the presence of a suitable catalyst, and optionally in the presence of an alcohol.

The process may be carried out in the presence of at least one suitable stabiliser. Preferably, the at least one stabiliser may be selected from hydroquinone, p-methoxyphenol, Topanol-A (2-t-butyl-4,6-dimethylphenol) or phenothiazine.

The term "alkyl" when used herein, means unless otherwise indicated, $C_1$ to $C_{10}$ alkyl and alkyl includes methyl, ethyl, propyl, butyl, pentyl, hexyl, and heptyl groups. Unless otherwise specified, alkyl groups may, when there is a sufficient number of carbon atoms, be linear or branched (particularly preferred branched groups include t-butyl and isopropyl), be saturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)R^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilicon groups, or mixtures thereof.

The term "Ar" or "aryl" when used herein, includes five- to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "alkenyl" when used herein, means $C_2$ to $C_{10}$ alkenyl and includes ethenyl, propenyl, butenyl, pentenyl, and hexenyl groups. Unless otherwise specified, alkenyl groups may, when there is a sufficient number of carbon atoms, be linear or branched, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined as for alkyl above and/or be interrupted by one or more (preferably less than 4) oxygen, sulphur, silicon atoms, or by silano or dialkylsilicon groups, or mixtures thereof.

Halo groups with which the above-mentioned groups may be substituted or terminated include fluoro, chloro, bromo and iodo.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term "hetero" as mentioned herein means nitrogen, oxygen, sulfur or mixtures thereof.

In a continuous process, after a period of, say, a few months, the efficacy of a sulphonic acid resin may have reduced to about 20% of its efficacy when fresh. This is often referred to as a "deactivated" resin. However, it has further been surprisingly found that the presence of a suitable source of formaldehyde in the present invention on a "deactivated" resin causes the removal of impurities at a rate similar to that of fresh resin.

Therefore, according to a second aspect of the present invention there is provided a process for purifying methyl methacrylate (MMA) comprising contacting liquid MMA having impurities therein with a sulphonic acid resin, in the presence of formaldehyde or a suitable source of methylene or ethylene of formula I as defined below:

where $R^5$ and $R^6$ are independently selected from $C_1$-$C_{12}$ hydrocarbons, preferably, $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H;

X is either O or S, preferably, O;

n is an integer from 1 to 100, preferably, 1 to 10, more preferably 1 to 5, especially, 1-3;

and m is 1 or 2, preferably 1, wherein the sulphonic acid resin is at least partially deactivated.

In a particularly preferred embodiment the compound of formula I is derived from formaldehyde in the presence of methanol and/or water. In such a case, the compound of formula I may be defined as a suitable source of formaldehyde. By the term "the sulphonic acid resin is at least partially deactivated", it is meant that the efficacy of the sulphonic acid resin has become reduced (as compared to a fresh resin) due to its prior exposure to resin contaminants such as those present in a feed stream being purified such as an impure liquid MMA stream.

Preferably, the at least partially deactivated sulphonic acid resin has less than 99.9% efficacy as compared to its efficacy when unused. Preferably, the at least partially deactivated sulphonic acid resin has less than 99% efficacy as compared to its efficacy when unused, more typically, less than 95% efficacy, most typically, less than 75% efficacy, especially, less than 50% efficacy.

Preferably, the at least partial deactivation refers to the sulphonic acid resins ability to react with at least one diene. For example, preferably the at least partially deactivated sulphonic acid resin has less than 50% efficacy in reacting with at least one diene as compared to its efficacy when unused.

According to a third aspect of the present invention there is provided methyl methacrylate such as liquid MMA having one or more of the impurities indicated herein which has contacted a sulphonic acid resin in the presence of formaldehyde or a suitable source of methylene or ethylene of formula I as defined below:

I where $R^5$ and $R^6$ are independently selected from $C_1$-$C_{12}$ hydrocarbons, preferably, $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H;

X is either O or S, preferably, O;

n is an integer from 1 to 100, preferably, 1 to 10, more preferably 1 to 5, especially, 1-3;

and m is 1 or 2, preferably 1, when in the liquid phase.

According to a fourth aspect of the present invention there is provided a polymer comprising methyl methacrylate residues, which methyl methacrylate residues have contacted a sulphonic acid resin in the presence of formaldehyde or a suitable source of methylene or ethylene of formula I as defined below:

I where $R^5$ and $R^6$ are independently selected from $C_1$-$C_{12}$ hydrocarbons, preferably, $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H;

X is either O or S, preferably, O;

n is an integer from 1 to 100, preferably, 1 to 10, more preferably 1 to 5, especially, 1-3;

and m is 1 or 2, preferably 1, when in the liquid monomer phase.

Preferably, the impure MMA of the present invention is produced by the condensation of formaldehyde with methyl propionate. It has been found that the present invention is particularly advantageous in the removal of impurities from liquid MMA produced by such a process. Typically, the impure MMA for purification by the practice of the present invention is produced by the condensation of formaldehyde with methyl propionate in the presence of a suitable basic catalyst and, optionally, methanol, to prevent acid formation. A suitable basic catalyst for the condensation reaction is an alkali metal doped silica such as Caesium on silica ($Cs^+$/$SiO_2$). In such cases, the silicas that may be employed are preferably porous high surface area silicas such as gel silicas, precipitated gel silicas and agglomerated pyrogenic silicas. Preferably, the alkali metal is present in the silica catalyst in the range 1-10% w/w (expressed as metal).

All of the features contained herein may be combined with any of the above aspects and in any combination.

The invention will now be illustrated by the following examples and with reference to the FIGURE in which:—

EXAMPLES

Example 1

100 g of water wet Lewatit 2314 strong sulphonic acid ion exchange resin supplied by Lanxess was washed by allowing methanol to flow down a glass column packed with the resin at a rate of 1 bed volume per hour until the eluent, initially brown, became colourless to the eye. It was then washed with pure MMA until the concentration of methanol fell to 100 ppm. 20 g of such resin was placed in a 3 necked round bottomed flask equipped with a magnetic stirrer follower, a thermometer and a water cooled reflux condenser. 50 ml of a sample of pure MMA to which 100 ppm of 2-methyl-1,5-hexadiene had been added was placed in the flask. The flask was placed in a preheated oil bath and samples taken by pipette from the flask at defined intervals. The same batch of resin was used for each experiment. Samples were analysed on a Varian GC equipped with a CPSil 1701 capillary column. The 2-methyl-1,5-hexadiene isomerised rapidly to form 2-methyl-2,5-hexadiene This component then disappeared very slowly to form 2-methyl-2,4-hexadiene. The experiment was run three times, at 70° C., 50° C. and 30° C. The wt % s of each component are shown in tables 1, 3 and 5.

Example 2

Example 1 was repeated, but in this case 1000 or 7000 ppm of 1,1-dimethoxymethane was added to the MMA solution before heating. The wt % s of each component are shown in tables 2, 4 and 6.

Example 3

Example 1 was repeated except that a mixture of 100 ppm each of 2,5-dimethyl-1,5-hexadiene and 2,5-dimethyl-2,4- hexadiene were used instead of 100 ppm 2-methyl-1,5 hexadiene. The wt % of each component at three different temperatures is shown in table 7, 9 and 11.

Example 4

Example 3 was repeated except that 1000 or 7000 ppm of 1,1-dimethoxymethane was added to the MMA solution before heating.

The wt % of each component at each heating temperature is shown in tables 8, 10 and 12.

Tables 7-12 show the amount of 2,5-dimethyl-2,4-hexadiene present at different time intervals and different temperatures both with and without 1,1-dimethoxymethane present.

TABLE 1

70° C., 0 ppm 1,1-dimethoxymethane

| Component | Time/min | | | | | |
|---|---|---|---|---|---|---|
| | 0 | 5 | 10 | 20 | 40 | 60 |
| 2Me-1,5-hexadiene | 0.0109% | 0.0000% | 0.0000% | 0.0000% | 0.0000% | 0.0000% |
| 2Me-2,5-hexadiene | 0.0000% | 0.0083% | 0.0072% | 0.0052% | 0.0031% | 0.0014% |
| Trans-2-Me-2,4-hexadiene | 0.0000% | 0.0005% | 0.0019% | 0.0022% | 0.0027% | 0.0025% |
| Cis-2-Me-2,4-hexadiene | 0.0000% | 0.0000% | 0.0000% | 0.0000% | 0.0000% | 0.0000% |

TABLE 2

70° C., 1000 ppm 1,1-dimethoxymethane

| Component | Time/min | | | | | |
|---|---|---|---|---|---|---|
| | 0 | 5 | 10 | 20 | 40 | 60 |
| 2Me-1,5-hexadiene | 0.0117% | 0.0007% | 0.0004% | 0.0005% | 0.0005% | 0.0006% |
| 2Me-2,5-hexadiene | 0.0000% | 0.0054% | 0.0027% | 0.0011% | 0.0009% | 0.0006% |
| Trans-2-Me-2,4-hexadiene | 0.0000% | 0.0000% | 0.0000% | 0.0000% | 0.0000% | 0.0000% |
| Cis-2-Me-2,4-hexadiene | 0.0000% | 0.0000% | 0.0000% | 0.0000% | 0.0000% | 0.0000% |

TABLE 3

50° C., 0 ppm 1,1-dimethoxymethane

| Component | Time/min | | | | | |
|---|---|---|---|---|---|---|
| | 0 | 5 | 10 | 20 | 40 | 60 |
| 2Me-1,5-hexadiene | 0.0109% | 0.0003% | 0.0004% | 0.0005% | 0.0000% | 0.0000% |
| 2Me-2,5-hexadiene | 0.0000% | 0.0076% | 0.0072% | 0.0068% | 0.0065% | 0.0049% |
| Trans-2-Me-2,4-hexadiene | 0.0000% | 0.0000% | 0.0000% | 0.0001% | 0.0003% | 0.0007% |
| Cis-2-Me-2,4-hexadiene | 0.0000% | 0.0000% | 0.0000% | 0.0000% | 0.0000% | 0.0000% |

TABLE 4

50° C., 1000 ppm 1,1-dimethoxymethane

| Component | Time/min | | | | | |
|---|---|---|---|---|---|---|
| | 0 | 5 | 10 | 20 | 40 | 60 |
| 2Me-1,5-hexadiene | 0.0111% | 0.0000% | 0.0000% | 0.0000% | 0.0000% | 0.0000% |
| 2Me-2,5-hexadiene | 0.0000% | 0.0062% | 0.0047% | 0.0031% | 0.0014% | 0.0008% |
| Trans-2-Me-2,4-hexadiene | 0.0000% | 0.0000% | 0.0000% | 0.0000% | 0.0000% | 0.0000% |
| Cis-2-Me-2,4-hexadiene | 0.0000% | 0.0000% | 0.0000% | 0.0000% | 0.0000% | 0.0000% |

TABLE 5

30° C., 0 ppm 1,1-dimethoxymethane

| Component | Time/min | | | | | |
|---|---|---|---|---|---|---|
| | 0 | 5 | 10 | 20 | 40 | 60 |
| 2Me-1,5-hexadiene | 0.0132% | 0.0002% | 0.0002% | 0.0002% | 0.0002% | 0.0001% |
| 2Me-2,5-hexadiene | 0.0000% | 0.0067% | 0.0070% | 0.0065% | 0.0065% | 0.0063% |
| Trans-2-Me-2,4-hexadiene | 0.0000% | 0.0000% | 0.0000% | 0.0000% | 0.0000% | 0.0000% |
| Cis-2-Me-2,4-hexadiene | 0.0000% | 0.0000% | 0.0000% | 0.0000% | 0.0000% | 0.0000% |

TABLE 6

30° C., 7000 ppm 1,1-dimethoxymethane

| Component | Time/min | | | | | |
|---|---|---|---|---|---|---|
| | 0 | 5 | 10 | 20 | 40 | 60 |
| 2Me-1,5-hexadiene | 0.0121% | 0.0007% | 0.0002% | 0.0002% | 0.0000% | 0.0000% |
| 2Me-2,5-hexadiene | 0.0000% | 0.0064% | 0.0052% | 0.0031% | 0.0009% | 0.0000% |
| Trans-2-Me-2,4-hexadiene | 0.0000% | 0.0000% | 0.0000% | 0.0000% | 0.0000% | 0.0000% |
| Cis-2-Me-2,4-hexadiene | 0.0000% | 0.0000% | 0.0000% | 0.0000% | 0.0000% | 0.0000% |

In the absence of 1,1-dimethoxymethane the 2-methyl-1,5-dimethylhexadiene rapidly isomerises to 2-methyl-2,5-hexadiene and then slowly converts in part to 2-methyl-2,4-hexadiene. In the presence of 1,1-dimethoxymethane, there is a rapid removal of 2-methyl-2,5-hexadiene following the isomerisation process, without 2-methyl-2,4-hexadiene being detected in the flask.

TABLE 7

30° C., 0 ppm 1,1-dimethoxymethane

| Component | Time/min | | | | | |
|---|---|---|---|---|---|---|
| | 0 | 5 | 10 | 20 | 40 | 60 |
| 2,5-Dimethyl-1,5-hexadiene | 0.0034% | 0.0000% | 0.0049% | 0.0027% | 0.0035% | 0.0034% |
| 2,5-Dimethyl-2,4-hexadiene | 0.0000% | 0.0000% | 0.0000% | 0.0060% | 0.0054% | 0.0044% |

TABLE 8

30° C., 7000 ppm 1,1-dimethoxymethane

| | Time/min | | | | | |
|---|---|---|---|---|---|---|
| Component | 0 | 5 | 10 | 20 | 40 | 60 |
| 2,5-dimethyl-1,5-hexadiene | 0.0069% | 0.0023% | 0.0024% | 0.0027% | 0.0023% | 0.0025% |
| 2,5-Dimethyl-2,4-hexadiene | 0.0082% | 0.0068% | 0.0039% | 0.0018% | 0.0000% | 0.0000% |

TABLE 9

50° C., 0 ppm 1,1-dimethoxymethane

| | Time/min | | | | | |
|---|---|---|---|---|---|---|
| Component | 0 | 5 | 10 | 20 | 40 | 60 |
| 2,5-dimethyl-1,5-hexadiene | 0.0082% | 0.0006% | 0.0009% | 0.0008% | 0.0008% | 0.0011% |
| 2,5-Dimethyl-2,4-hexadiene | 0.0088% | 0.0111% | 0.0119% | 0.0118% | 0.0120% | 0.0117% |

TABLE 10

50° C. 1000 ppm 1,1-dimethoxymethane

| | Time/min | | | | | |
|---|---|---|---|---|---|---|
| Component | 0 | 5 | 10 | 20 | 40 | 60 |
| 2,5-dimethyl-1,5-hexadiene | 0.0057% | 0.0013% | 0.0016% | 0.0015% | 0.0017% | 0.0016% |
| 2,5-Dimethyl-2,4-hexadiene | 0.0064% | 0.0090% | 0.0071% | 0.0047% | 0.0018% | 0.0013% |

TABLE 11

70° C. 0 ppm 1,1-dimethoxymethane

| | Time/min | | | | | |
|---|---|---|---|---|---|---|
| Component | 0 | 5 | 10 | 20 | 40 | 60 |
| 2,5-dimethyl-1,5-hexadiene | 0.0024% | 0.0005% | 0.0006% | 0.0006% | 0.0010% | 0.0012% |
| 2,5-Dimethyl-2,4-hexadiene | 0.0042% | 0.0133% | 0.0131% | 0.0124% | 0.0104% | 0.0096% |

TABLE 12

70° C. 1000 ppm 1,1-dimethoxymethane

| | Time/min | | | | | |
|---|---|---|---|---|---|---|
| Component | 0 | 5 | 10 | 20 | 40 | 60 |
| 2,5-dimethyl-1,5-hexadiene | 0.0027% | 0.0013% | 0.0010% | 0.0008% | 0.0007% | 0.0003% |
| 2,5-Dimethyl-2,4-hexadiene | 0.0049% | 0.0050% | 0.0027% | 0.0014% | 0.0009% | 0.0006% |

In the absence of 1,1-dimethoxymethane the rapid isomerisation of 2,5-dimethyl-2,5-hexadiene to 2,5-dimethyl-2,4-hexadiene is followed by a very slow decay of the latter. When 1,1-dimethoxymethane is present in the solution there is a rapid decay of 2,5-dimethyl-2,4-hexadiene to a different product.

The first order rate constants for decay of 2-methyl-2,5-hexadiene and 2,5-dimethyl-2,4-hexadiene are listed in the table 13 for each of the conditions.

TABLE 13

| | [1,1-dimethoxymethane]/ppm | First Order Rate Constant $s^{-1}$ | | |
|---|---|---|---|---|
| | | 30° C. | 50° C. | 70° C. |
| rate constants for decay of 2-methyl-2,5-hexadiene | 0 | | 0.0015 | 0.007 | 0.0325 |
| | 1000 | | 0.0367 | 0.1147 |
| | 7000 | 0.0581 | | |
| rate constants for decay of 2,5-dimethyl-2,4-hexadiene | 0 | 0.0003 | 0.0063 | 0.0003 |
| | 1000 | | 0.0365 | 0.0812 |
| | 7000 | 0.0878 | | |

Therefore, the addition of 1,1-dimethoxymethane has a large impact on the rate of decay both for the 2-methyl 2,5-hexadiene and 2,5-dimethyl-2,4-hexadiene.

Example 5

Two Lewatit 2431 resin samples were used:
A Fresh Resin
This was prepared by washing the resin with methanol containing 200 ppm hydroquinone (HQ) and then pure MMA containing 100 ppm HQ.
B Used Resin
A sample which had been exposed to a continuous flow of impure MMA over a period of 12 days was used. The impure MMA was derived from a process generating MMA by a condensation reaction between methyl propionate and formaldehyde.

The two samples were tested with a reaction mixture of impure MMA and containing the levels of cis and trans-2-methyl-2,4-hexadiene shown in the table and 100 ppm HQ, using the method of example 1 and at 50° C.:

The concentrations of each species are shown in table 14 below.

TABLE 14

| | | | Time of Exposure/minutes | | | | | |
|---|---|---|---|---|---|---|---|---|
| | | | 0 | 2 | 5 | 10 | 20 | 30 |
| Fresh Resin | 0 ppm 1,1-Dimethoxymethane | t-2-Me-2,4-hexadiene | 0.0035% | 0.0011% | 0.0004% | 0.0002% | 0.0000% | 0.0000% |
| | | c-2-Me-2,4-hexadiene | 0.0040% | 0.0003% | 0.0001% | 0.0001% | 0.0000% | 0.0000% |

TABLE 14-continued

| | | | \multicolumn{6}{c}{Time of Exposure/minutes} |
|---|---|---|---|---|---|---|---|---|
| | | | 0 | 2 | 5 | 10 | 20 | 30 |
| Used Resin | 0 ppm 1,1-Dimethoxymethane | t-2-Me-2,4-hexadiene | 0.0035% | 0.0022% | 0.0021% | 0.0016% | 0.0007% | 0.0002% |
| | | c-2-Me-2,4-hexadiene | 0.0040% | 0.0014% | 0.0008% | 0.0007% | 0.0003% | 0.0001% |
| Fresh Resin | +1000 ppm 1,1-Dimethoxymethane | t-2-Me-2,4-hexadiene) | 0.0041% | 0.0008% | 0.0000% | 0.0000% | 0.0000% | 0.0000% |
| | | c-2-Me-2,4-hexadiene | 0.0015% | 0.0004% | 0.0000% | 0.0000% | 0.0000% | 0.0000% |
| Used Resin | +1000 ppm 1,1-Dimethoxymethane | t-2-Me-2,4-hexadiene) | 0.0041% | 0.0001% | 0.0000% | 0.0000% | 0.0000% | 0.0000% |
| | | c-2-Me-2,4-hexadiene | 0.0015% | 0.0000% | 0.0000% | 0.0000% | 0.0000% | 0.0000% |

The change in concentration of the 2-methyl hexadienes with time is complicated by their being in equilibrium in the presence of the acidic ion exchange resin. Therefore, the concentrations of the dienes were added to examine the decay kinetics. It was found that their combined concentrations fell approximately exponentially with time. The first order rate constants derived from the two resins, with and without added formaldehyde containing species are shown in table 15 below:

TABLE 15

| Kinetic Comparison | Fresh Resin | Used Resin |
|---|---|---|
| No 1,1-dimethoxymethane | 0.5 | 0.09 |
| Added 1,1-dimethoxymethane | 0.8 | 0.9 |

Over the fresh resin, there was an approximately 50% increase in rate of removal on addition of 1,1-dimethoxymethane. Over the resin that had been used previously, the rate of removal in the absence of 1,1-dimethoxymethane was very low, only 17% of that on the fresh resin. However, there was a ten fold increase in activity on the used resin in the presence of 1,1-dimethoxymethane, such that the activity was as good as that on the fresh resin.

This experiment demonstrates that addition of formaldehyde is particularly effective on partially deactivated acidic ion exchange resins.

Example 6

A sample of MMA containing cis and trans 2-methyl-2,4-hexadiene and other impurities and 100 ppm HQ was passed as a liquid over a fixed bed of 16 g resin in a 0.5 inch OD stainless steel reactor at atmospheric pressure and 70° C. The flow rate was adjusted to give a residence time of 31.7 minutes. After the feed was introduced, the samples were left for 2 residence times before samples were collected and analysed. The analysis of the combined levels of cis and trans 2-methyl-2,4-dimethylhexadiene is compared with the untreated MMA containing stream in table 16.

TABLE 16

| Formalin Source | start | 80 ppm HCHO | 200 ppm HCHO | 320 ppm HCHO |
|---|---|---|---|---|
| | | | Fresh Resin | |
| 1,1-dimethoxymethane | 0.0061% | 0.0005% | 0.0005% | 0.0000% |
| 37% formalin | 0.0061% | 0.0012% | 0.0000% | 0.0000% |
| Process stream containing 81.5% MeP, 10% HCHO, 6.5% methanol, 2% others | 0.0061% | 0.0007% | 0.0006% | 0.0000% |
| | | | Used Resin | |
| 1,1-dimethoxymethane | 0.0061% | 0.0018% | 0.0017% | 0.0000% |
| 37% formalin | 0.0061% | 0.0026% | 0.0004% | 0.0004% |
| Process stream containing 81.5% MeP, 10% HCHO, 6.5% methanol, 2% others | 0.0061% | 0.0014% | 0.0015% | 0.0006% |

This experiment demonstrates that there is no difference between whether the formaldehyde is added as 1,1-dimethoxymethane, as formalin or as a methanolic non-aqueous formaldehyde stream.

Example 7

A bed of 750 ml of Lewatit 2431 Acidic Ion Exchange Resin was used for treating impure MMA containing various impurities and 100 ppm hydroquinone as stabiliser at a flow rate of 600 g/hour. The flow was maintained for 62 days. During the first 62 days, the average feed and exit compositions in ppm for various impurities and fractional conversions are shown in table 17 for a formaldehyde feed of 17.5 ppm:

TABLE 17

| | Feed | Exit | Conversion |
|---|---|---|---|
| Isobutyraldehyde | 96.1 | 37.4 | 61.1% |
| Methacrolein | 3.2 | 0.1 | 96.4% |
| Isobutanol | 50.7 | 27.7 | 45.3% |
| Pentenal | 8.9 | 0.2 | 97.4% |
| Toluene | 18.9 | 17.6 | 7.1% |

Further impurities were analysed after longer flow periods as shown in table 18.

TABLE 18

| Day 120-126 | Feed | Exit | Average Conversion |
|---|---|---|---|
| Ethylisopropenylketone | 2.7 | 0.0 | 100.0% |

Figure 1:
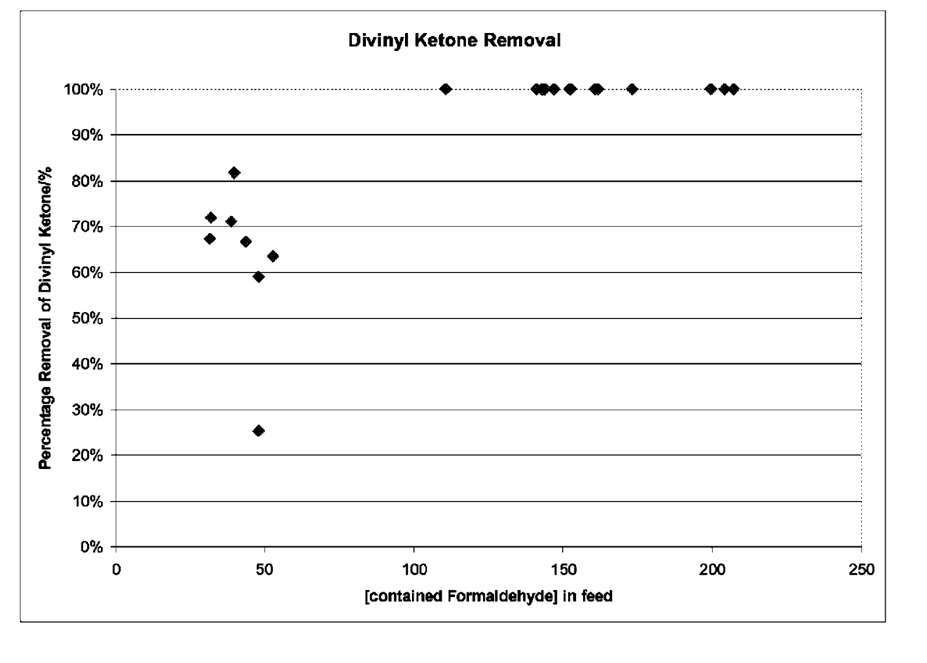
FIG. 1 is a graph of divinylketone removal with respect to formaldehyde feed.

Several other components require formaldehyde for their removal when the resin bed has been operating for a long time. FIG. 1 and table 19 show that divinyl ketone (DVK) containing MMA requires over 60 ppm of formaldehyde before it is completely removed.

TABLE 19

| Time on Line/ days | Contained Formaldehyde/ ppm | Fractional conversion of Divinyl ketone/% |
|---|---|---|
| 115 | 32 | 67% |
| 116 | 32 | 72% |
| 116 | 39 | 71% |
| 117 | 40 | 82% |
| 117 | 44 | 67% |
| 118 | 48 | 25% |
| 118 | 48 | 59% |
| 119 | 53 | 63% |
| 119 | 111 | 100% |
| 120 | 200 | 100% |
| 120 | 207 | 100% |
| 121 | 204 | 100% |
| 121 | 173 | 100% |
| 122 | 162 | 100% |
| 122 | 143 | 100% |
| 123 | 141 | 100% |
| 123 | 144 | 100% |
| 124 | 143 | 100% |
| 124 | 153 | 100% |
| 125 | 147 | 100% |
| 125 | 152 | 100% |
| 126 | 161 | 100% |

Example 8

A fresh ion exchange resin (800 ml aliquot) was washed with methanol to remove water at a flow rate of 0.15 g/ml/h, until the water content fell to below 0.2 wt %. It was then drained to remove excess methanol and washed with MMA at the same flow rate until the methanol level dropped below 0.2 wt %. Two volumes of impure MMA containing 111 ppm diethylketone and 320 ppm formal-2 ($CH_3$—O—($CH_2$—O)$_2$—$CH_3$), (equivalent to 180 ppm contained formaldehyde) to be used for the experiment were then flushed through the resin sample at 2 ml/min for 80 min to replace the pure MMA with the desired component. The resin was transferred into a bottle, the bottle was topped up with the impure MMA sample and the sample was sparged with air through a cannula to saturate it. The bottle was sealed and then placed in an oil bath at 55° C. Periodically, samples were collected for analysis. The analysis is shown in table 20:

TABLE 20

| Time exposed to Resin in hours | [Diethylketone]/ppm |
|---|---|
| 0.0 | 111 |
| 0.7 | 103.5 |
| 2.5 | 102.5 |
| 3.8 | 95 |
| 4.8 | 91 |
| 5.8 | 110 |
| 6.3 | 70 |
| 8.0 | 66 |
| 9.5 | 55 |
| 11.7 | 31 |
| 14.75 | 37 |
| 15.5 | 38 |

Clearly, the process of the invention results in a dramatic reduction in the level of diethyl ketone.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for purifying methyl methacrylate (MMA) comprising:
   contacting liquid MMA having impurities therein with a sulphonic acid resin, in the presence of $CH_2O$ or a compound of formula I,
   wherein formula I is:

I wherein $R^5$ and $R^6$ are independently selected from $C_1$-$C_{12}$ hydrocarbons or H;
   X is O;
   n is an integer from 1 to 100; and
   m is 1 or 2; and
   obtaining purified MMA.

2. A process for purifying methyl methacrylate (MMA) according to claim 1, wherein the compound of formula I is a suitable source of formaldehyde.

3. A process for purifying methyl methacrylate according to claim 2, wherein $CH_2O$ or the amount of formaldehyde that can be liberated from the suitable source of formaldehyde is present in an amount between 0.01 and 0.1 weight percent relative to the weight of liquid MMA.

4. A process for purifying methyl methacrylate according to claim 2, wherein the suitable source of formaldehyde is selected from 1,1 dimethoxymethane, higher formals of formula $CH_3\text{—}O\text{—}(CH_2\text{—}O)_i\text{—}CH_3$ where i=2 or more, formalin or a mixture comprising formaldehyde, methanol and methyl propionate.

5. A process for purifying methyl methacrylate according to claim 1, wherein the $CH_2O$ or compound of formula I is mixed with the impure liquid MMA prior to contact with the sulphonic acid resin.

6. A process for purifying methyl methacrylate according to claim 5, wherein in a continuous or semi-continuous process, the impure liquid MMA stream is mixed with a stream containing the $CH_2O$ or compound of formula I to form a combined liquid stream prior to contact with the sulphonic acid resin.

7. A process for purifying methyl methacrylate according to claim 6, wherein the $CH_2O$ or compound of formula I is present in an amount between 0.01 and 0.1 weight percent in the combined liquid stream.

8. A process for purifying methyl methacrylate according to claim 1, wherein the compound of formula I is alternatively or additionally present as an impurity in the MMA.

9. A process for purifying methyl methacrylate according to claim 8, wherein the impurity in the MMA is formal-2 $(CH_3\text{—}O\text{—}(CH_2\text{—}O)_2\text{—}CH_3)$.

10. A process for purifying methyl methacrylate according to claim 1, wherein the purification process of the invention is performed at a temperature between 25 and 100° C.

11. A process for purifying methyl methacrylate according to claim 1, wherein at least one carboxylic acid ester is also present in the purification process.

12. A process for purifying methyl methacrylate according to claim 11, wherein in a continuous or semi-continuous process the at least one carboxylic acid ester is already present in the impure liquid MMA stream prior to contact with the sulphonic acid resin.

13. A process for purifying methyl methacrylate according to claim 1, wherein the impurities have a boiling point within 15° C. of that of MMA.

14. A process for purifying methyl methacrylate according to claim 1, wherein the impurities are selected from isobutyraldehyde, either as isobutyraldehyde or in a compound which regenerates isobutyraldehyde when exposed to the sulphonic acid ion exchange resin, optionally substituted $C_6\text{-}C_{20}$ trienes, optionally substituted unsaturated aldehydes and ketones, divinyl ketone, ethyl vinyl ketone, diethyl ketone, ethyl isopropenyl ketone, 3-methylene 1-hexen-4-one, methacrolein, isobutanol, toluene, and pentenals such as 3-pentenal.

15. A process for purifying methyl methacrylate according to claim 1, wherein the process is carried out in the presence of at least one suitable stabilizer.

16. A process for purifying methyl methacrylate (MMA) comprising:
contacting liquid MMA having impurities therein with a sulphonic acid resin, in the presence of $CH_2O$ or a compound of formula I,
wherein formula I is wherein $R^5$ and $R^6$ are independently selected from $C_1\text{-}C_{12}$ hydrocarbons or H;
X is O;
n is an integer from 1 to 100; and
m is 1 or 2;
wherein the sulphonic acid resin is at least partially deactivated; and
obtaining purified MMA.

17. A process for purifying methyl methacrylate (MMA) comprising:
contacting liquid MMA having impurities therein with a sulphonic acid resin, in the presence of a compound of formula I,
wherein formula I is wherein $R^5$ and $R^6$ are independently selected from $C_1\text{-}C_{12}$ hydrocarbons or H;
X is O;
n is an integer from 1 to 100; and
m is 1 or 2; and
obtaining purified MMA.

18. A process for purifying methyl methacrylate according to claim 17, wherein the liquid MMA further comprises $CH_2O$.

* * * * *